United States Patent [19] [11] 3,984,452
Wiersum et al. [45] Oct. 5, 1976

[54] PROCESS FOR THE PREPARATION OF A P,P'-DICYANOBIBENZYL AND A M,M'-DICYANOBIBENZYL

[75] Inventors: Ulfert Elle Wiersum, Velp; Joannes Dominicus Bik, Eerbeek, both of Netherlands

[73] Assignee: Akzona Incorporated, Asheville, N.C.

[22] Filed: Apr. 11, 1975

[21] Appl. No.: 567,311

[30] Foreign Application Priority Data
Apr. 25, 1974 Netherlands............... 7405550

[52] U.S. Cl................ 260/465 H; 260/453 A; 260/453 AR; 260/464; 260/468 G; 260/475 R; 260/514 G; 260/515 P; 260/563 R; 260/570.5 P; 260/578
[51] Int. Cl.²........................ C07C 121/64

[58] Field of Search............ 260/465 H, 670

[56] References Cited
UNITED STATES PATENTS
3,646,018  2/1972  Duke, Jr. et al............. 260/670 X OTHER PUBLICATIONS
Suhr et al.: Chemical Abstracts, vol. 75, p. 200, (1971).

*Primary Examiner*—Lewis Gotts
*Assistant Examiner*—Dolph H. Torrence
*Attorney, Agent, or Firm*—Stevens, Davis, Miller & Mosher

[57] ABSTRACT p-Tolunitrile or m-tolunitrile is dimerized at an elevated temperature in the gaseous phase with a residence time of less than 0.1 second to form p,p'-dicyanobibenzyl or m,m'-dicyanobibenzyl.

13 Claims, 1 Drawing Figure

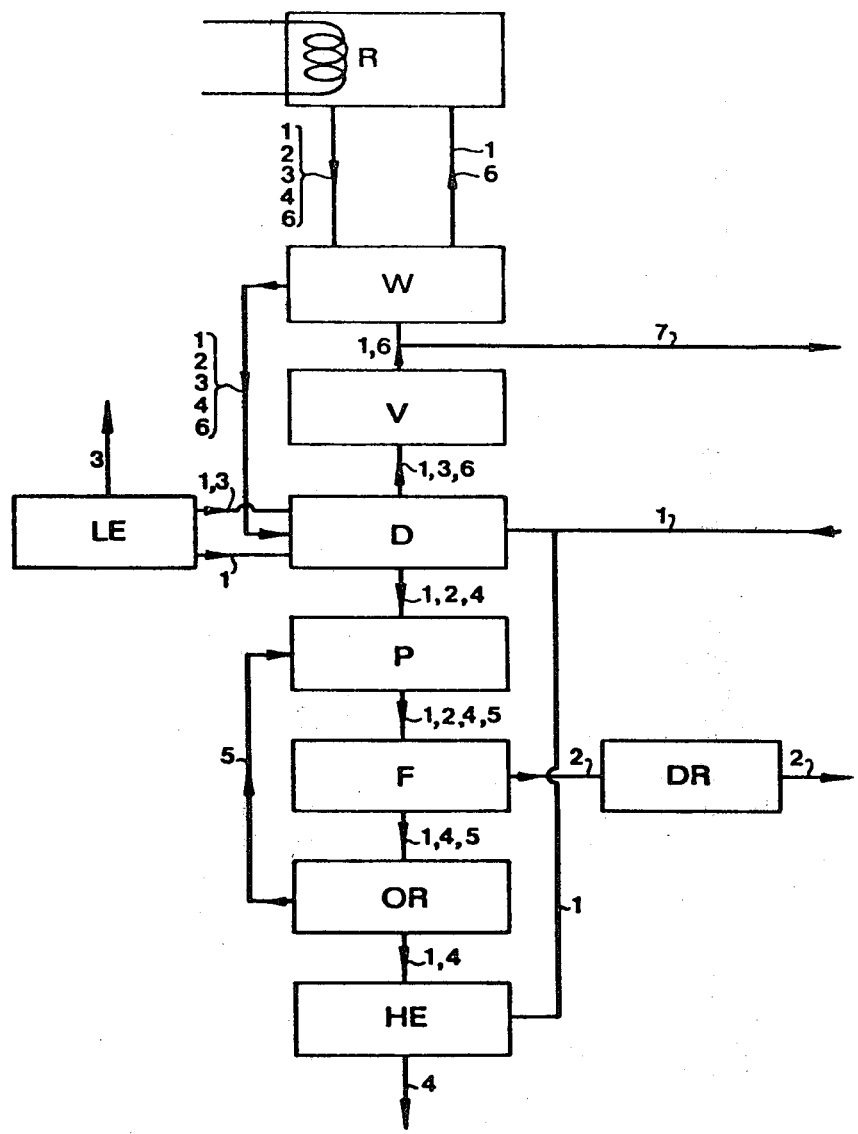

PROCESS FOR THE PREPARATION OF A P,P'-DICYANOBIBENZYL AND A M,M'-DICYANOBIBENZYL

This invention relates to a process for the preparation of a p,p'-dicyanobibenzyl and a m,m'-dicyanbibenzyl by dimerization at elevated temperature of a corresponding p-tolunitrile and m-tolunitrile, respectively.

A process of the type indicated above has been proposed in the French Pat. No. 2,048,838. According to the process described in this patent specification the dimerization is carried out under oxidative conditions and in the presence of iodine and a catalyst which contains chromite and at a temperature in the range of 149° to 704° C. The residence time is always at least 2 seconds. The greatest drawback of this process is that instead of pure bibenzyl a mixture of bibenzyl and unsaturated stilbene is always obtained. Technologically, these products are difficult to separate. Moreover, the bibenzyl yield is relatively small because of the simultaneous formation of stilbene.

It is an object of the present invention to provide a process of the above-indicated type which no longer has the disadvantage of giving a high percentage of by-products and whose yield, calculated on converted monomer, is generally more than 80%.

Other objects of the invention will become apparent from the following description with reference to the accompanying drawing which is a block diagram of an apparatus suitable for conducting the reaction in accordance with an embodiment of the invention.

In accordance with this invention a process in the form of a high-temperature gas phase reaction and a residence time of less than 0.1 second is provided. The suprising element of the invention follows from the fact that in a recent article in Aust. J. Chem. 25, 149–170 (1972), p. 164, on the pyrolysis of m-tolunitrile and p-tolunitrile it is mentioned that at 850° C. no change could be detected.

In an article in J. Am. Chem. Soc. 90, 2839–2842 (1968), which especially deals with the preparation of bibenzyl and compounds derived therefrom by pyrolysis in the gas phase, the possibility of preparing p,p-dicyanobibenzyl by pyrolysis of p-tolunitrile in the gas phase is not even mentioned.

From a discussion in this article it does appear that the preparation of p-p'-dicyanobibenzyl can probably best be carried out by pyrolysis in the gas phase. This process has the disadvantage, however, that the starting product must be prepared via the roundabout route of benzyl alcohol and the oxalic ester thereof. Another disadvantage is that in this pyrolysis the yield is not more than 44%.

Finally, it should be added than an article in Synthesis 426 (1971) describes the preparation of dicyanobibenzyl by dimerization of the corresponding tolunitrile. However, the dimerization is not effected then by pyrolysis in the gas phase, but is the result of a reaction in the plasma of a glow discharge.

Because of the high yield, the simplicity of the process and the fact that the formed by-products can readily be isolated the last-mentioned method has been recommended as the most attractive known way of preparing dicyanobibenzyl. For use on an industrial scale, however, this method seems not quite so attractive on account of its very high capital investment and energy cost. In the same article reference is made to various other processes for the preparation of dicyanobibenzyl, such as the oxidative dimerization, the reaction of cyanohalides with Grignard-compounds or the multi-stage synthesis from toluene or 1,2-diphenyl-ethane. As regards these known processes it should be added that in all cases the yield is small and a large amount of by-product is formed. No mention is made of the possibility of dimerizing tolunitrile by using a high-temperature gas phase process.

The process according to the invention not only permits using a readily available and relatively inexpensive starting material, but also has the advantage that when it is to be applied on an industrial scale, its capital investment need not be immoderately high. Moreover, apart from the by-product, whose volatility is higher or lower than that of the monomer, being obtained in small amounts, it can readily be isolated from the desired endproduct.

For carrying out the process according to the invention use may be made of m-tolunitrile or p-tolunitrile or derivatives thereof, one or more hydrogen atoms of the phenyl group being replaced with thermally resistant substituents; it is preferred, however, to use p-tolunitrile or m-tolunitrile. The temperature at which the reaction proceeds best is in the range of 600°–900° C., and preferably in the range of 750°–850° C. Higher temperatures may be used if desired. However, the reaction will be less selective then. The starting product may be mixed, if desired, with inert gases or vapors such as nitrogen, hydrogen or noble gases and the like, but it is preferred to use superheated steam. If desired also traces may be present of compounds such as sulfur compounds ($CS_2$), chlorine or chlorinated compounds ($CCl_4$), which form radicals at the reaction temperature. A catalyst may also be present.

The pressure at which the reaction is carried out is not critical. It has been found that good results are obtained both at an absolute pressure of only a few mm Hg and at an absolute pressure of 1 atmosphere.

The reaction may be carried out in any suitable manner, for instance by passing the tolunitrile through a tube heated to the desired temperature. The tube will generally be of some metal, but it may also be of some ceramic or other material. If desired, the tube may contain obstacles in the form of, for instance, Raschig rings, metal shavings, etc.. The residence time of the reaction mixture in the reactor forms an essential factor in the process of the invention.

In order to be insured of good selectivity, the residence time should always be less than 0.1 second. In practice it is often found to remain considerably below it.

The isolation of the dicyanobibenzyl formed may be carried out in one of several suitable ways. Although the amount of converted monomer per pass is relatively small (about 0.2%), it is preferred to concentrate the dimer prior to further purification.

In one method for isolating the dimer from the monomer, the reaction mixture is cooled down to a temperature between the melting point of the dimer and the boiling point of the monomer and the solid dimer deposits on the wall of the apparatus and can be removed.

For use on an industrial scale it will generally be preferred to use a process in which the reaction is carried out cyclically in such a way that the reaction mixture leaving the reactor is cooled by the transfer of heat to the gas stream flowing into the reactor and condensed, and the monomer is isolated therefrom by distillation and recycled. For the isolation and purification of the dimer the invention provides a process in which the dimer accumulated after a number of cycles is isolated from the condensate by precipitation in a non-solvent for the dimer and a solvent for the monomer and subsequent filtration.

It has been found that good results are obtained if an aliphatic alcohol having 1–4 C atoms, methanol, ethanol, propanol or butanol or a ketone is used as a solvent. It is preferred to use methanol; but in practice acetone is also found to give satisfactory results. The cyano groups of the 1,2-di(cyanophenyl) ethane can in a known and usual way be converted into for instance: —COOH, —NH$_2$, —CH$_2$NH$_2$, —NCO, —CH$_2$NCO or COOR (when R is alkyl and by preference t-butyl) groups, and the phenyl groups may be converted or not into cyclohexyl groups by hydrogenation. The resulting compounds can be applied as starting materials for initiators and cross-linking agents to be used in the preparation of polymers; the compounds can also be used as starting materials for polymers.

The invention will be elucidated in the following examples, which of course do not limit the scope of the invention.

EXAMPLE I

On a laboratory scale 100 ml of p-tolunitrile were evaporated from a flask at a pressure of 5–30 Torr and passed through a quartz tube 2 cm in diameter and 25 cm long at a rate of 5–10 ml per minute. Subsequently, the reaction mixture was successively passed through a condenser and fed back to the flask. This treatment was continued for 24 hours, after which of the mixture formed in the flask the non-converted tolunitrile was evaporated off the residue (20 g) was poured into a three- or fourfold amount of methanol. The p,p'-dicyanobibenzyl then precipitated and was filtered off. The yield was 15 g. The melting point was between 200° and 204°C. According to gas chromatographic analysis of the mixture leaving the quartz tube about 0.2% of the starting nitrile had been converted, the selectivity being 91%. After re-crystallization from chlorobenzene the melting point of the purified end-product was 203°–204°C.

EXAMPLE II

Example I was repeated. Instead of p-tolunitrile, however, m-tolunitrile was used. After re-crystallization from chlorobenzene the endproduct (20 g) has a melting point of 161°–162°C. Per pass about 0.2% of the tolunitrile was converted, the selectivity being 86%.

EXAMPLE III

Example I is repeated. Here, however, steam is used as carrier gas. The partial pressure of the tolunitrile is 100–500 mm Hg. Noteworthy in this experiment is that no carbon deposits at all. The selectivity is about the same as in Example I, whereas the conversion has gone up to 0.5%.

EXAMPLE IV

With reference to the accompanying block diagram, this example indicates how the reaction can be carried out in the event of an annual production from p-tolunitrile of 100 tons of p,p'-dicyanobibenzyl. The reaction is carried out with steam as a carrier gas. The molar ratio steam/tolunitrile is 5/1, and a pressure of 1 atmosphere is used. The yield is 80%, calculated on converted nitrile, and the conversion is 0.2% per pass. The flow rates are given kg/h. In this diagram the letter R refers to the reactor, which has a volume of 200 liters and may be filled with packing in order to promote the transfer of heat. A number of heating coils run through the reactor with which the temperature inside the reactor is kept at about 850° C. The reaction mixture leaving the reactor R is composed of tolunitrile 1, dicyanbibenzyl 2, light constituents 3, heavy constituents 4, steam 6 and gaseous constituents 7 and is subsequently passed through a heat exchanger W having a heat exchanging surface area of about 150 m$^2$ and from there to the distillation column D. From this column D part of the more volatile components 1,3,6 is passed to a unit LE, where the volatile constituents 3 are isolated from tolunitrile 1 and steam 6, after which the steam is fed back to the distillation column D. Also the supply of fresh tolunitrile 1 (18 kg/h) takes place via the distillation column D. Between the heat exchanger W and the distillation column D there is a fan V, which serves to keep up the circulating process.

Between the heat exchanger W and the fan V a provision is made to discharge any accumulated by-products 7. From the distillation column D tolunitrile 1 (85 kg/h), dimer 2, (15 kg/h) heavy constituents 4 (3 kg/h) are fed to the precipitation unit P, which contains at least a three-fold excess of methanol 5. The resulting slurry is passed through a filter F, which retains the solid dicyanobibenzyl 2 (15 kg/h); after the latter has been treated in a dried DR it is separated as such. The filtrate composed of tolunitrile 1, heavy constituents 4 and methanol 5 is passed to a solvent regeneration unit OR, where the methanol 5 is distilled off from the constituents having a higher boiling point and fed back to the precipitation unit P. The tolunitrile 1 and the heavy constituents 4 are subsequently isolated by distillation in a distillation column HE; here the heavy constituents 4 (3 kg/h) are discharged and the tolunitrile 1 is fed back to the distillation column D. The heavy constituents 4 contain about 30–50% p,p'-dicyanodiphenylmethane and α-(p-cyanobenzyl)benzylcyanide.

Although the invention has been described in detail for the purpose of illustration, it is to be understood that such detail is solely for the purpose and the variations can be made by those skilled in the art without departing from the spirit and scope of the invention except as it may be limited by the claims.

What is claimed is:

1. A process for the preparation of a p,p'-dicyanobibenzyl or a m,m'-dicyanobibenzyl which comprises dimerizing the corresponding p-tolunitrile or m-tolunitrile in a high-temperature gas phase reaction which produces a dimer in a residence time of less than 0.1 second.

2. The process according to claim 1 wherein the reaction is carried out at a temperature in the range of 600° to 900° C.

3. The process of claim 1 wherein the reaction temperature is 750° to 850° C.

4. The process of claim 1 wherein the reaction is carried out in the presence of a carrier gas.

5. The process of claim 4 wherein the carrier gas is superheated steam.

6. The process of claim 1 wherein the reaction is carried out is a reactor and cyclically is such a way that the reaction mixture leaving the reactor is cooled by the transfer of heat to the gas stream flowing into the reactor and condensed, and the monomer is isolated therefrom by distillation and recycled.

7. The process of claim 6 wherein the resulting dimer accumulated after a number of cycles is isolated from the condensate by precipitation in a non-solvent for the dimer and a solvent for the monomer and subsequent filtration.

8. The process of claim 7 wherein the solvent is an aliphatic alcohol with 1–4 C-atoms.

9. The process of claim 6, wherein the solvent is acetone.

10. A process which comprises heating a p-tolunitrile or m-tolunitrile in a gaseous phase at a temperature of at least about 600° C to form the corresponding p,p'-dicyanobibenzyl or a m,m'-dicyanobibenzyl in less than 0.1 second.

11. The process of claim 1 wherein the p-tolunitrile or m-tolunitrile is unsubstituted or substituted only with groups which are thermally stable at the reaction temperature.

12. The process of claim 1 wherein the compound which is dimerized is p-tolunitrile or m-tolunitrile.

13. The process of claim 10 wherein the p-tolunitrile or m-tolunitrile is unsubstituted or substituted only with groups which are thermally stable at a temperature of 600° to 900° C.

* * * * *